(12) United States Patent
Dixon et al.

(10) Patent No.: US 8,513,200 B2
(45) Date of Patent: Aug. 20, 2013

(54) PROCESS FOR RELAXING OR STRAIGHTENING HAIR, USING WEAK DICARBOXYLIC ACIDS WITH HEAT

(75) Inventors: Felicia Dixon, Chicago, IL (US); Bradford Pistorio, Chicago, IL (US); Angela Ellington, Flossmoor, IL (US); Ming Yee, Chicago, IL (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/126,635

(22) PCT Filed: Oct. 28, 2009

(86) PCT No.: PCT/EP2009/064168
§ 371 (c)(1),
(2), (4) Date: Jun. 16, 2011

(87) PCT Pub. No.: WO2010/049434
PCT Pub. Date: May 6, 2010

(65) Prior Publication Data
US 2011/0256084 A1    Oct. 20, 2011

Related U.S. Application Data

(60) Provisional application No. 61/109,252, filed on Oct. 29, 2008, provisional application No. 61/109,267, filed on Oct. 29, 2008.

(51) Int. Cl.
*A61K 38/00*    (2006.01)

(52) U.S. Cl.
USPC .......................................................... 514/20.7

(58) Field of Classification Search
None
See application file for complete search history.

(56) References Cited

U.S. PATENT DOCUMENTS

| | | | | |
|---|---|---|---|---|
| 4,228,810 A | * | 10/1980 | Moore et al. .................. | 132/204 |
| 5,101,841 A | * | 4/1992 | Crews et al. .................. | 132/203 |
| 7,178,531 B2 | * | 2/2007 | Carballada et al. .......... | 132/224 |
| 2006/0127337 A1 | | 6/2006 | Radisson | |
| 2008/0223392 A1 | | 9/2008 | Cannell et al. | |

FOREIGN PATENT DOCUMENTS

CN    101268991 A    9/2008

* cited by examiner

*Primary Examiner* — Anand Desai
*Assistant Examiner* — Melissa Mercier
(74) *Attorney, Agent, or Firm* — Novak Druce Connolly Bove + Quigg LLP

(57) ABSTRACT

A process for straightening or relaxing hair comprising the following steps: (a) providing a hair straightening or relaxing composition having a pH ranging from 8 to 11.5, and containing, in a cosmetically acceptable medium, at least one weak acid chosen from monocarboxylic, dicarboxylic and tricarboxylic acids, their salts, and mixtures thereof; (b) contacting the hair with the hair straightening or relaxing composition to form treated hair; and (c) straightening or relaxing the treated hair by applying heat, wherein hydroxide-containing compounds are not used. Disclosed herein is also a preferred hair straightening or relaxing composition.

14 Claims, No Drawings

PROCESS FOR RELAXING OR STRAIGHTENING HAIR, USING WEAK DICARBOXYLIC ACIDS WITH HEAT

CROSS REFERENCE TO RELATED APPLICATIONS

This application is a National Phase filing under 35 U.S.C. §371 of PCT/EP2009/064168 filed on Oct. 28, 2009; and this application claims the benefit of Provisional Application No. 61/109,252 filed on Oct. 29, 2008 and Provisional Application No. 61/109,267 filed on Oct. 29, 2008 under 35 U.S.C. §119(e); the entire contents of all are hereby incorporated by reference.

BACKGROUND OF THE INVENTION

Hair straightening or hair relaxing products have been commercially available for over fifty years for people who want straighter, more manageable hair. Most commercially available hair relaxers are composed of a strong hydroxide base that has been found to compromise the quality of hair.

Commercial products based only on alkaline metal hydroxides such as sodium hydroxide and lithium hydroxide are typically used to straighten or relax curly hair. There are primarily four different types of hydroxide-containing hair straighteners: sodium hydroxide, potassium hydroxide, lithium hydroxide, and guanidine hydroxide. The straightening product is usually applied quickly and can only remain in the hair for a very limited amount of time. Due to the alkalinity of such products, if the product is not rinsed from the hair at the appropriate time, damage to the hair can occur, as well as chemical burns to the scalp and areas surrounding the hair.

Thus, the objective of the present invention is to provide a hair straightening or relaxing process which is safer than, yet as effective as, conventional processes.

Another object of the present invention is to provide a hair straightening or relaxing composition and a process that provides desirable and permanent/long-lasting hair straightening effects in a short period of application time.

BRIEF SUMMARY OF THE INVENTION

The present invention is directed to a process for straightening or relaxing hair involving the steps of:
(a) providing a hair straightening or relaxing composition having a pH ranging from 8 to 11.5, and containing, in a cosmetically acceptable medium, at least one weak acid chosen from monocarboxylic, dicarboxylic and tricarboxylic acids, their salts, and mixtures thereof;
(b) contacting the hair with the hair straightening or relaxing composition to form treated hair; and
(c) straightening or relaxing the treated hair by applying heat, wherein hydroxide-containing compounds are not used.

Preferably, the hair straightening or relaxing composition used in step (a) has a pH of from 8 to 11, and more preferably of at least 9.

According to a first preferred embodiment, the hair straightening or relaxing composition used in step (a) further contains at least one viscosity modifying agent.

According to a second preferred embodiment, the hair straightening or relaxing composition used in step (a) further contains at least one denaturant capable of disrupting hydrogen bonds in the hair.

According to a third preferred embodiment, the hair straightening or relaxing composition used in step (a) further contains at least one pH adjusting agent.

The present invention is also directed to a gel composition for straightening or relaxing hair having a pH ranging from 8 to 11.5 and containing, in a cosmetically acceptable medium:
 at least one weak acid chosen from monocarboxylic, dicarboxylic and tricarboxylic acids, their salts, and mixtures thereof, and
 at least one viscosity modifying agent.
 the Gel Composition of the Present Invention can also contain at least one denaturant as defined above, and/or at least one pH adjusting agent.

Such a composition does not contain hydroxide-containing compounds. Furthermore, such a composition allows to straighten or relax the hair without using hydroxide-containing compounds.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

As used herein, the terms "straightening" or "straighten" or "relaxing" or "relax" the hair mean to remove the curl from the hair or reduce the degree of curl of the hair. It also means changing the shape of hair or the degree of curl in the hair to make the hair more straight.

It has been surprisingly found that by employing the composition and process of the present invention, straightening or relaxing of the hair can be achieved in the absence of hydroxide-containing compounds, such as sodium hydroxide, which are conventionally used to effectuate hair straightening and relaxing. Indeed, and this is one important feature and advantage of the present invention, hydroxide-containing compounds are not used at all in the process of the present invention. Thus, the present invention facilitates the straightening or relaxing of hair in a manner that is less irritating and damaging to a user's skin and hair.

Without intending to be bound by theory, it is believed that a chemical reaction occurs between the carboxylic acid group(s) of the at least one weak acid and the amine groups present in the hair keratin, resulting in the formation of a stable amide bond. Heat is believed to be used to further facilitate this chemical reaction which causes a physical change within the hair, resulting in straighter or more relaxed hair fibers.

Conventional products, which employ hydroxide-containing compounds, have a tendency to cause both skin irritation and damage to the hair, due to the presence of the hydroxide compounds in said products. However, by employing a weak acid product, preferably in a viscous form, combined with heat and, optionally, means for physically smoothing the hair, satisfactory and long-lasting straightening or relaxing of the hair can be achieved in a very short period of time and in a manner that is safer for both skin and hair.

Weak Acids

Suitable weak monocarboxylic acids for use in the present invention are generally those having a pKa of from 0.5 to 8, preferably from 2 to 6, and more preferably from 2.5 to 5.

Examples of suitable weak monocarboxylic acids include, but are not limited to aryl, (hetero)cyclic, alkyl, and/or aliphatic monocarboxylic acids such as for example acetic acid, mono, di or tri chloroacetic acid, glyoxylic acid, glycolic acid, acrylic acid, methacrylic acid, pyruvic acid, propionic acid, D-gluconic acid, and D-galacturonic acid.

A structural example of a monocarboxylic acid suitable for use in the present invention is shown in formula (I) below:

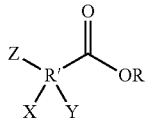

(I)

in which:
R denotes H, $Li^+$, $Na^+$, $K^+$, or $NH_4^+$;
R' denotes an alkyl, alkylene, aryl, cyclic or heterocyclic group containing up to 12 carbon atoms, and which can contain intermittent heteroatoms such as nitrogen and oxygen; and
X, Y and Z, which may be identical or different, denote H, OH, OR (where R is as defined above or denotes $CH_2$), $NH_2$, or a halogen atom, or
X and Y denote one unique oxygen atom, Z being as defined above.

Aryl and (hetero)cyclic monocarboxylic acids are in particular compounds comprising a carboxylic acid moiety on a saturated or unsaturated single or multiple ring containing 5 to 12 carbon atoms which can further contain intermittent nitrogen or oxygen atoms, such as a for example lactam or lactone. Substituents on the ring(s) may include —H, =O, —OH, —OR, —$NH_2$ halides, or combinations thereof.

Suitable weak dicarboxylic acids for use in the present invention are those having a $pKa_1$ or a $pKa_2$ of from 1 to 10, preferably from 1 to 7, and more preferably from 1.5 to 5.

Examples of suitable weak dicarboxylic acids include, but are not limited to aryl, (hetero)cyclic, alkyl, and/or aliphatic dicarboxylic acids.

Suitable representatives thereof include malic acid, maleic acid, itaconic acid, oxalic acid, malonic acid, mesoxalic acid, fumaric acid, succinic acid, tartaric acid, alpha-ketoglutaric acid, iminodiacetic acid, galactartic acid, adipic acid, glutaric acid, their salts, and mixtures thereof.

A structural example of a dicarboxylic acid suitable for use in the present invention is shown in formula (II) below:

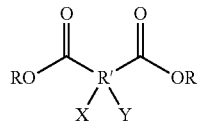

(II)

in which
R denotes H, $Li^+$, $Na^+$, $K^+$, or $NH_4^+$;
R' denotes an alkyl, alkylene, aryl, cyclic or heterocyclic group containing up to 12 carbon atoms, and which can contain intermittent heteroatoms such as nitrogen and oxygen; and
X and Y, which may be identical or different, denote H, OH, OR (where R is as defined above or denotes $CH_3$), $NH_2$, or a halogen atom, or
X and Y denote one unique oxygen atom.

Aryl and (hetero)cyclic dicarboxylic acids are in particular compounds comprising two carboxylic acid moieties on a saturated or unsaturated single or multiple ring containing 5 to 12 carbon atoms which can further contain intermittent nitrogen or oxygen atoms, such as a for example lactam or lactone. Substituents on the ring(s) may include —H, =O, —OH, —OR, —$NH_2$ halides, or combinations thereof.

Particularly preferred weak dicarboxylic acids include malic acid, maleic acid, itaconic acid, adipic acid, and glutaric acid, their salts, and mixtures thereof.

Suitable weak tricarboxylic acids for use in the present invention are those having a $pKa_1$, a $pKa_2$ or a $pKa_3$ of from 1 to 10, preferably from 2 to 6 and more preferably from 2.5 to 5.

Examples of suitable weak tricarboxylic acids include, but are not limited to aryl, alkyl or aliphatic tricarboxylic acids such as citric, domoic or nitrilotriacetic acids.

A structural example of a tricarboxylic acid suitable for use in the present invention is shown in figure (III) below:

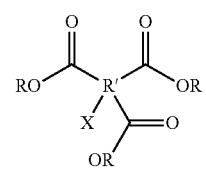

(III)

in which
R denotes H, $Li^+$, $Na^+$, $K^+$, or $NH_4^+$;
R' denotes an alkyl, alkylene, aryl, cyclic or heterocyclic group containing up to 12 carbon atoms, and which can contain intermittent heteroatoms such as nitrogen and oxygen; and
X denotes H, OH, OR (where R is as defined above or denotes $CH_3$), $NH_2$, or a halogen atom.

Aryl and (hetero)cyclic tricarboxylic acids are in particular compounds comprising three carboxylic acid moieties on a saturated or unsaturated single or multiple ring containing 5 to 12 carbon atoms which can further contain intermittent nitrogen or oxygen atoms, such as a for example lactam or lactone. Substituents on the ring(s) may include —H, =O, —OH, —OR, —$NH_2$, halides, or combinations thereof.

The weak acid chosen from monocarboxylic acids, dicarboxylic acids, tricarboxylic acids, their salts, and mixtures thereof is typically employed in the hair straightening or relaxing composition in an amount of from 0.1% to 50% by weight, preferably from 0.5% to 20%, more preferably from 0.5% to 10% by weight, even more preferably from 1% to 5% by weight, based on the total weight of the composition.

Particularly preferred weak acids for use in the compositions of the present invention are dicarboxylic acids, and in particular those chosen from malic acid, maleic acid, itaconic acid, adipic acid, glutaric acid, their salts, and mixtures thereof.

Viscosity Modifying Agents

The viscosity modifying agents for use in the present invention may be any agent capable of changing the viscosity, thickness or rheology of a composition, such as in particular gelling agents and thickening agents.

The viscosity modifying agent may be selected in particular from gelling agents in polymeric or organic form, and gelling agents in mineral or inorganic form.

For the purposes of the present invention an "inorganic gelling agent" is a gelling agent whose principal structural elements are devoid of carbon atoms. However, these gelling agents may also include carbon derivatives as secondary or modifying structural elements. As an example of such inorganic gelling agents mention may be made of clays modified with fatty acid salts, as described below.

In contrast, in the context of the present invention, organic gelling agents will be defined as being agents whose principal structural elements include at least one carbon atom. As examples of such agents mention may be made of polyorganosiloxanes, silicone gums or polyurethanes, as defined below.

In one embodiment the at least one viscosity modifying agent is a gelling agent which is not soluble in water, and in particular is a liquid-fatty-phase gelling agent.

Such a liquid-fatty-phase gelling agent can be selected, in particular, from agents that gel via chemical crosslinking, physical crosslinking, hydrophobic and/or hydrogen-bonding interactions.

Examples of gels obtained by chemical crosslinking are the organopolysiloxanes sold or manufactured under the names KSG6 by Shin-Etsu, Trefil E-505C or Trefil E-506C from Dow Corning, Gransil from Grant Industries (SR-CYC, SR DMF10, SR-DC556) or those sold in the form of preconstituted gels (KSG15, KSG17, KSG16, KSG18 and KSG21 from Shin-Etsu, Gransil SR 5CYC gel, Gransil SR DMF 10 gel, Gransil SR DC556 gel, SF 1204 and JK 113 from General Electric.

Examples of gels obtained by physical crosslinking are silicone gums, such as for example the product sold or manufactured under the name 761 by Rhone-Poulenc (Rhodia Chimie).

Examples of gels obtained by hydrophobic and hydrogen-bonding interactions are gelling agents selected in particular from aminosilicone polymers having triazinyl groups or pyrimidinyl groups attached to the amino groups, non-silicone polyamides whose ends carry ester or triamide functions, polyurethanes, and (meth)acrylic and/or vinylic polymers which carry side groups able to give rise to mutual hydrophobic and hydrogen-bonding interactions.

The gelling agents may also be selected from copolymers such as the polystyrene-silicone or the polyethylene-silicone, copolymers comprising a silicone sequence and another sequence, or graft, which is polyvinylic or poly(meth)acrylic, polymers or copolymers resulting from the polymerization or copolymerization of an ethylenic monomer containing one or more ethylenic bonds, which are preferably conjugated (or dienes), polymers or copolymers resulting from the polymerization or copolymerization of an ethylenic monomer. In particular, it is possible to use vinylic, acrylic or methacrylic copolymers. The ethylenic gelling agent may comprise, for example, a styrene (S) block or an alkylstyrene (AS) block and a block selected from ethylene/butylene (EB), ethylene/propylene (EP), butadiene (B), isoprene (I), acrylate (A), methacrylate (MA) blocks or a combination of these blocks.

The gelling agent can also be a copolymer comprising at least one styrene block. A triblock copolymer, and in particular those of polystyrene/polyisoprene or polystyrene/polybutadiene type, such as those sold or manufactured under the name "Luvitol HSB" by BASF and those of the polystyrene/copoly(ethylene-propylene) type or, alternatively, those of polystyrene/copoly(ethylene/butylene) type, such as those sold or manufactured under the brand name "Kraton" by Shell Chemical Co. or Gelled Permethyl 99A by Penreco, may be used. Styrene-methacrylate copolymers may also be used.

As an ethylenic gelling agent that can be used in the compositions in accordance with the invention, mention may be made, for example, of the following commercial products: Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58, Gelled Permethyl 99A-753-59, Versagel 5970 and Versagel 5960 from Penreco, and OS 129880, OS 129881 and OS 84383 from Lubrizol (styrene-methacrylate copolymer). Diblocks or triblocks or polystyrene-copoly(ethylene/butylene) are likewise included in the present invention.

Gelling agents such as fat-soluble polymers having liquid-crystal groups are also suitable for the preparation of cosmetic compositions according to the present invention. In particular, fat-soluble polymers whose skeleton is of silicone, vinylic and/or (meth)acrylic type, and which possess liquid-crystal side groups, can be used advantageously.

According to another particular embodiment, the liquid-fatty-phase gelling agent may also be in mineral or inorganic form.

In particular, the liquid-fatty-phase gelling agent may be a non-crystalline, non-silicone gelling agent.

Preferred examples of mineral gelling agent include modified clays, and silicas.

Modified clays useful as a gelling agent in the present invention are preferably chosen from hectorites modified with an ammonium chloride of a $C_{10}$ to $C_{22}$ fatty acid, such as: hectorite modified with distearyldimethylammonium chloride (also known as quaternium-18 bentonite), which is sold or manufactured under the names Bentone 34 by Elementis Specialties, and Claytone SO and Claytone 40 by Southern Clay; modified clays known under the name of quaternium-18/benzalkonium bentonites which are sold or manufactured by Southern Clay under the names Claytone HT, Claytone GR and Claytone PS; clays modified with stearyldimethyl-benzoylammonium chloride (also known as stearalkonium bentonites), which is sold or manufactured under the names Claytone APA and Claytone AF by Southern Clay, and Baragel 24 by Rheox.

Silicas useful as mineral gelling agent in the present invention include in particular pyrogenic silica, and preferably those which are hydrophobically modified. The pyrogenic silica may have a particle size which may be nanometric or micrometric, ranging for example from 5 nm to 200 nm.

Pyrogenic silicas may be obtained by high-temperature hydrolysis of a volatile compound of silicon in an oxyhydrogen flame, producing a finely divided silica. This process allows hydrophilic silicas to be obtained which possess a substantial number of silanol groups on their surface. The silanol groups may be replaced, for example, by hydrophobic groups, thereby giving rise to a hydrophobic silica.

The hydrophobic groups may be:

trimethylsiloxyl groups, which are obtained in particular by treating pyrogenic silica in the presence of hexamethyldisilazane. The silicas thus treated are known as "silica silylate." They are sold or manufactured, for example, under the references "Aerosil R812" by Degussa and "Cab-O-Sil TS-530" by Cabot;

dimethylsilyloxyl or polydimethylsiloxane groups, which are obtained in particular by treating pyrogenic silica in the presence of polydimethyldisiloxane or dimethyldichlorosilane. The silicas thus treated are known as "silica dimethylsilylate" according to the CTFA (6th edition, 1995); They are sold or manufactured, for example, under the references "Aerosil R972" and "Aerosil R974" by Degussa and "Cab-O-Sil TS-610" and "Cab-O-Sil TS-720" by Cabot;

groups derived from the reaction of pyrogenic silica with silane alkylates or siloxanes. These treated silicas are, for example, the products sold or manufactured under the reference "Aerosil R805" by Degussa.

When the composition of the present invention comprises an aqueous phase, the gelling agent may be an aqueous-phase gelling agent.

The gelling agent for the aqueous phase that may be used in the cosmetic compositions according to the invention can, in particular, be characterized by its capacity to form, in water, above a certain concentration, a gel. This composition may vary widely depending on the nature of the gelling agent in question.

The gelling agent could be a water-soluble gelling polymer and is therefore present in the aqueous phase of the composition in solubilized form.

More particularly, this aqueous-phase gelling polymer may be selected from the following and their mixtures thereof:

homopolymers or copolymers of acrylic or methacrylic acid or their salts and their esters, and in particular the products sold under the names "Versicol F" or "Versicol K" by Allied Colloid, "Ultrahold 8" by Ciba-Geigy, and polyacrylic acids of Synthalen K type; and polyacrylic acid/alkyl acrylate copolymers sold under the name Pemulen;

copolymers of acrylic acid and acrylamide, such as those sold in the form of their sodium salt under the names "Reten" by Hercules, the sodium polymethacrylate sold under the name "Darvan N degrees 7" by Vanderbilt, and the sodium salts of polyhydroxycarboxylic acids that are sold under the name "Hydagen F" by Henkel;

AMPS (polyacrylamidomethylpropane sulfonic acid) homo- and co-polymers, such as: AMPS partially neutralized with ammonia and highly crosslinked, sold for example sold by Clariant; AMPS/acrylamide copolymers such as the Sepigel or Simulgel products sold by SEPPIC; the AMPS/polyoxyethylenated alkyl methacrylate copolymers (crosslinked or non-crosslinked) such as Aristoflex HMS, sold by Clariant.

Other examples of water-soluble gelling polymers are:

proteins, such as proteins of plant origin, for instance wheat proteins and soy proteins; proteins of animal origin such as keratins, for example keratin hydrolysates and sulphonic keratins;

anionic, cationic, amphoteric or nonionic chitin or chitosan polymers;

cellulose polymers such as hydroxyethylcellulose, hydroxypropylcellulose, methylcellulose, ethylhydroxyethylcellulose, carboxymethylcellulose, and quaternized cellulose derivatives;

vinylic polymers, such as polyvinylpyrrolidones, copolymers of methyl vinyl ether and malic anhydride, the copolymer of vinyl acetate and crotonic acid, copolymers of vinylpyrrolidone and vinyl acetate; copolymers of vinylpyrrolidone and caprolactam; polyvinyl alcohol;

polymers of natural origin, optionally modified, such as: gum arabics, guar gum and its derivatives such as hydroxypropylguar, xanthan gum and its derivatives, scleroglucan gum, karaya gum, carouba gum, alginates, gelatins, carrageenans, sclerotium gum, glycoaminoglycans, shellac resin, gum sandarac, dammar, elemis and copal resins, deoxyribonucleic acid, mucopolysaccharides such as hyaluronic acid and its derivatives, chondroitin sulphates, and mixtures thereof.

Suitable thickening agents for use in the present invention include anhydrous aluminum silicate, fumed silica, hydrated magnesium aluminum silicate and colloidal clays.

Suitable hydrophilic thickening agents include carboxyvinyl polymers, such as the Carbopols (carbomers) and the Pemulens (acrylate/C10-C30 alkyl acrylate copolymer); the terpolymer of methacrylic acid, methyl acrylate and dimethyl (meta-isopropenyl)benzyl isocyanate of ethoxylated alcohol (Polyacrylate-3), such as the product marketed by Amerchol under the trademark Viscophobe DB 1000; polyacrylamides, such as the crosslinked copolymers marketed under the trademarks Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by Seppic; optionally crosslinked and/or neutralized polymers and copolymers of 2-acrylamido-2-methylpropanesulfonic acid, such as the poly(2-acrylamido-2-methylpropanesulfonic acid) marketed by Clariant under the trademark "Hostacerin AMPS" (CTFA name: ammonium polyacryldimethyltauramide).

Suitable lipophilic thickening agents include synthetic polymers, such as the poly(C10-C30 alkyl acrylate) marketed under the trademark "Doresco IPA 13-1" by Landec, and modified clays, such as hectorite and its derivatives such as those marketed under the Bentone names.

Further suitable rheology modifying agents include fatty acid amides such as coconut diethanolamide and monoethanolamide, and oxyethylenated monoethanolamide of carboxylic acid alkyl ether, and associative polymers.

According to a preferred embodiment of the present invention, the viscosity modifying agent is chosen from anionic, cationic, amphoteric, and nonionic associative polymers.

Suitable anionic associative polymers are for example crosslinked terpolymers formed from acrylic or methacylic acid, alkyl acrylates or methacrylates, and allyl ether comprising a fatty chain. Preferred representatives thereof are the crosslinked terpolymers of methacrylic acid, of ethyl acrylate, and of polyethylene glycol (10 EO) stearyl alcohol ether (Steareth-10), for example, those sold by the company Allied Colloids under the names Salcare SC 80 and Salcare SC 90, which are aqueous 30% emulsions of a crosslinked terpolymer of methacrylic acid, of ethyl acrylate and of steareth-10 alkyl ether (40/50/10).

Other non-limiting examples of preferred anionic associative polymers include the polymers formed from acrylic acid as main monomer, $C_{10}$-$C_{30}$ alkyl acrylates and a reticulating agent, such as the products sold by the company Goodrich under the trade names Pemulen TR1, Pemulen TR2, and Carbopol 1382 and the product sold by the company SEPPIC under the name Coatex SX. A particular preferred product is the polymer sold under the name Pemulen TR1.

Other examples of suitable anionic associative polymers are maleic anhydride/C30-C38 alpha-olefin/alkyl maleate terpolymers, such as the product (maleic anhydride/$C_{30}$-$C_{38}$ alpha-olefin/isopropyl maleate copolymer) sold under the name Performa V 1608 by the company Newphase Technologies; acrylic terpolymers, such as a methacrylic acid/methyl acrylate/behenyl alcohol dimethyl-meta-isopropenylbenzylisocyanate ethoxylated (40 EO) terpolymer, for example as an aqueous 25% dispersion.

Another type of suitable anionic associative polymers include copolymers comprising among their monomers a carboxylic acid containing alpha, beta-monoethylenic unsaturation and an ester of a carboxylic acid containing alpha, beta-monoethylenic unsaturation and of an oxyalkylenated fatty alcohol. A non-limiting example of a compound of this type is Aculyn 22 sold by the company Rohm and Haas, which is a methacrylic acid/ethyl acrylate/oxyalkylenated stearyl methacrylate terpolymer.

Suitable cationic associative polymers include, but are not limited to:

(I) cationic associative polyurethanes, which can be formed from diisocyanates and from various compounds having at least one function containing a labile hydrogen. The functions containing a labile hydrogen may be chosen from alcohol, primary and secondary amine, and thiol functions, giving, after reaction with the diisocyanate functions, polyurethanes, polyureas, and polythioureas, respectively. The expression "polyurethanes" which can be used according to the present invention encompasses these three types of polymer, namely polyurethanes per se, polyureas and polythioureas, and also copolymers thereof. Example of such compounds include, but are not limited to, methylenediphenyl diisocyanate, methylenecyclohexane diisocyanate, isophorone diisocyanate, tolylene diisocyanate, naphthalene diisocyanate, butane diisocyanate, and hexane diisocyanate.

(II) quaternized cellulose derivatives, and (III) polyacrylates containing non-cyclic amine side groups.

The quaternized cellulose derivatives include in particular:

quaternized celluloses modified with groups comprising at least one fatty chain, such as alkyl, arylalkyl, and alkylaryl groups comprising at least 8 carbon atoms, and mixtures thereof; and quaternized hydroxyethylcelluloses modified with groups comprising at least one fatty chain, such as alkyl, arylalkyl, and alkylaryl groups comprising at least 8 carbon atoms, and mixtures thereof.

The alkyl radicals born by the above quaternized celluloses or hydroxyethylcelluloses preferably comprises from 8 to 30 carbon atoms, and the aryl radicals may be chosen from phenyl, benzyl, naphthyl, and anthryl groups.

Examples of quaternized alkylhydroxyethylcelluloses containing $C_8$-$C_{30}$ fatty chains include, for instance, the products Quatrisoft LM 200, Quatrisoft LM-X 529-18-A, Quatrisoft LM-X 529-18B (C12 alkyl), and Quatrisoft LM-X 529-8 (C18 alkyl) sold by the company Amerchol, and the products Crodacel QM, Crodacel QL (C12 alkyl) and Crodacel QS (C18 alkyl) sold by the company Croda.

The amphoteric associative polymers may be chosen, for example, from those comprising of at least one non-cyclic cationic unit. Examples of preferred amphoteric associative polymers according to the present invention are the acrylic acid/(meth)acrylamidopropyltrimethyl-ammonium chloride/stearyl methacrylate terpolymers.

The nonionic associative polymers that may be used according to the present invention may be chosen from:

(I) celluloses modified with groups comprising at least one fatty chain; for example:

hydroxyethylcelluloses modified with groups comprising at least one fatty chain, such as alkyl, arylalkyl, and alkylaryl groups, and mixtures thereof, and in which the alkyl groups contain preferably from 8 to 22 carbon atoms, such as for instance the product Natrosol Plus Grade 330 CS(C16 alkyls) sold by the company Aqualon, and the product Bermocoll EHM 100 sold by the company Berol Nobel, those modified with alkylphenyl polyalkylene glycol ether groups, such as the product Amercell Polymer HM-1500 (nonylphenyl polyethylene glycol (15) ether) sold by the company Amerchol.

(II) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc.

(III) copolymers of vinylpyrrolidone and of fatty-chain hydrophobic monomers; for example:

the products Antaron V216 or Ganex V216 (vinylpyrrolidone/hexa-decene copolymer) sold by the company I.S.P.;

the products Antaron V220 or Ganex V220 (vinylpyrrolidone/eicosene copolymer) sold by the company I.S.P.

(IV) copolymers of C1-C6 alkyl methacrylates or acrylates and of amphiphilic monomers comprising at least one fatty chain, for example, the methyl acrylate/oxyethylenated stearyl acrylate copolymer sold by the company Goldschmidt under the name Antil 208.

(V) copolymers of hydrophilic methacrylates or acrylates and of hydrophobic monomers comprising at least one fatty chain, for example, the polyethylene glycol methacrylate/lauryl methacrylate copolymer.

(VI) polyurethane polyethers comprising in their chain both hydrophilic blocks usually of polyoxyethylenated nature and hydrophobic blocks which may be aliphatic sequences alone and/or cycloaliphatic and/or aromatic sequences.

(VII) polymers with an aminoplast ether skeleton containing at least one fatty chain, such as the Pure Thix compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for at least one pendent chain to be included. In addition, the polymer may comprise a hydrocarbon-based chain at one end or at both ends of a hydrophilic block.

The polyurethane polyethers may be multiblock, for example, in triblock form. Hydrophobic blocks may be at each end of the chain (for example: triblock copolymer with a hydrophilic central block) or distributed both at the ends and in the chain (for example: multiblock copolymer). These polymers may also be chosen from graft polymers and starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers may comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

Examples of nonionic fatty-chain polyurethane polyethers that may be used include: Rheolate 205 containing a urea function, sold by the company Rheox, as well as Rheolate 208, 204, and 212; Acrysol RM 184 sold by the company Rohm and Haas; the product Elfacos T210 containing a $C_{12}$-$C_{14}$ alkyl chain, and the product Elfacos T212 containing a $C_{18}$ alkyl chain, sold by the company Akzo. The product DW 1206B from Rohm and Haas containing a C20 alkyl chain and a urethane linkage, sold at a solids content of 20% in water, may also be used.

It is also possible to use solutions or dispersions of these polymers, for example, in water or in aqueous-alcoholic medium. Examples of such polymers include, but are not limited to Rheolate 255, Rheolate 278 and Rheolate 244 sold by the company Rheox, and the products DW 1206F and DW 1206J sold by the company Rohm and Haas.

In at least one embodiment, the polyurethane polyether may be chosen from those that may be obtained by polycondensation of at least three compounds comprising of: (i) at least one polyethylene glycol comprising from 150 to 180 mol of ethylene oxide, (ii) stearyl alcohol or decyl alcohol, and (iii) at least one diisocyanate.

Such polyurethane polyethers are sold, for example, by the company Rohm and Haas under the names Aculyn 44 and Aculyn 46 [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%)

and water (81%); Aculyn 44 is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%)].

According to the present invention, the particularly preferred viscosity modifying agents are the following:

(a) cationic polymers, and in particular polyquaternium-37;

(b) polysaccharides or polysaccharide derivatives and in particular:

celluloses and derivatives thereof, such as hydroxyalkyl cellulose polymers and alkyl hydroxyalkyl cellulose polymers such as hydroxyethyl cellulose, hydroxypropyl cellulose, cetyl hydroxyethyl cellulose; methyl cellulose and its derivatives such as carboxymethyl cellulose hydroxymethylcellulose derivatives such as hydroxypropyl methylcellulose and hydroxybutyl methyl cellulose, quaternized celluloses and hydroxyethylcelluloses;

natural or synthetic gums, and in particular xanthan gum, guar gum;

starch and starch derivatives;

(c) homopolymers and copolymers of carboxyvinyl monomers, and in particular homopolymers and copolymers of (meth)acrylic acid, such as: polyacrylic acid, acrylic acid/ ethyl acrylate copolymers, acrylic acid/polyallyl sucrose copolymers.

According to a particularly preferred embodiment, the viscosity modifying agents is polyquaternium-37. Such a polymer is for example commercially available from Cognis under the trademark name Ultragel 300 and from Ciba under the trademark name Salcare.

The viscosity modifying agent(s) is (are) employed in an amount sufficient to provide the inventive composition with a viscosity such that when the composition is applied to hair, the composition does not easily drip down the hair fibers in a fluid-like manner and it is able to hold the fibers together during the treatment or application period. At the same time, the viscosity of the inventive composition is such that it is easy to spread or apply onto the hair fibers in a uniform manner.

The viscosity modifying agent(s) may be used in concentrations ranging from 0.1% to 10.0% by weight, preferably from 0.5% to 5.0% by weight, even more preferably from 1.0% to 5.0% by weight of the total weight of the composition.

Denaturant

The hair straightening or relaxing composition can further contain at least one denaturant, capable of disrupting hydrogen bonds in the hair.

Such denaturant may for example be employed in the event increased hair straightening/relaxing efficacy is desired.

Examples of suitable denaturants include, but are not limited to guanidine carbonate; halide, sulfate, or phosphate derivatives of guanidine; urea; alkyl or cyclic derivatives of urea; and mixtures thereof.

The denaturant, if used, is typically employed in the hair straightening or relaxing composition in an amount of from 0.1% to 25% by weight, preferably from 0.5% to 10% by weight, and more preferably from 1% to 5% by weight, based on the total weight of the composition.

pH Adjuster

A pH adjusting agent capable of yielding a pH range of from 8 to 11.5, and preferably, of from 8 to 11, and more preferably a pH value of greater than 9 and up to 11, with respect to the hair straightening or relaxing composition, can be employed.

Examples thereof include carbonate, bicarbonate, phosphate, and borate salts of various alkali and alkali earth metals such as sodium, lithium or calcium, respectively. Preferred representative thereof are in particular sodium carbonate, sodium bicarbonate, sodium phosphate, sodium borate, and mixtures thereof.

Further suitable pH adjusting agents include primary, secondary and tertiary amines. Preferred representatives thereof include monoethanol amine (MEA), 2-amino-2-methyl-propanol (AMP), 2-butylethanol amine (BEA), triethanolamine (TEA), N,N-dimethylethanolamine (DMEA), and N,N-bis (2-hydroxyethyl)glysine.

Additionally, other suitable pH adjusting agents are sulfonic acid compounds which include for example 3-[(1,1-dimethyl-2-hydroxyethyl)amino]-2-hydroxypropane-sulfonic acid (AMPSO), 2-[N-cyclohexylamino] ethanesulfonic acid (CHES), 4-[cyclohexylamino]-1-butanesulfonic acid (CABS), 3-[cyclohexylamino]-1-propanesulfonic acid (CAPS), 3-[cyclohexylamino]-2-hydroxy-1-propanesulfonic acid CAPSO, N-[2-hydroxyethyl]piperazine-N'-[4-butanesulfonic acid] (HEPBS), N-tris[hydroxymethyl]methyl-4-aminobutanesulfonic acid (TABS), or N-tris[hydroxymethyl]methyl-3-aminopropanesulfonic acid (TAPS), and mixtures thereof.

Cosmetically Acceptable Medium

As used herein, the term "cosmetically acceptable medium" is known to one of ordinary skill in the art, and comprises preferably water and/or at least one organic solvent.

The compositions of the present invention may also advantageously contain emulsifiers such as for example glyceryl stearate, glycol stearate, self-emulsifying waxes, emulsifying silicones, fatty alcohols, and fatty acids.

According to one preferred embodiment, the hair straightening or relaxing composition disclosed herein is in the form of a gel, a liquid gel, a gel cream, a gel lotion or gel mousse so as to keep the hair fibers together in a smooth position during the leave-in time.

Adjuvants

The hair straightening or relaxing composition as disclosed herein may also comprise at least one adjuvant chosen, for example, from silicones in soluble, dispersed and microdispersed forms; nonionic, anionic, cationic and amphoteric surfactants; ceramides, glycoceramides and pseudoceramides; vitamins and provitamins including panthenol; waxes; water-soluble or liposoluble, silicone-based and non-silicone-based sunscreens; nacreous agents and opacifiers; sequestering agents; plasticizers; solubilizers; acidifying agents; mineral and organic thickeners; natural and synthetic oils; antioxidants; hydroxy acids; penetrating agents; fragrances; preserving agents; and mixtures thereof.

In the event that surfactants are employed in the composition of the present invention, said composition may be used as a shampoo. Similarly, in the event that the composition of the invention is intended to be used as a hair conditioner, various types of conditioning agents can be added to the composition in order to increase his hair treating property.

After the straightening or relaxing step (c), the process of the present invention can advantageously comprise a step of rinsing the treated hair, and/or a step of washing the treated hair followed by rinsing thereof.

According to another embodiment of the present invention, there is provided a process for straightening or relaxing hair involving the steps of: (a) contacting the hair with the above-disclosed hair straightening or relaxing composition for a length of time sufficient to penetrate the fiber; and (b)

straightening or relaxing the treated hair using heat to remove a desired degree of curl from the hair and, optionally, physically smoothing hair.

Smoothing of hair treated with the above-disclosed hair straightening or relaxing composition involves using a combination of heat and optionally, means for physically smoothing the hair. The heat necessary to effectuate smoothing should be at least 50° C.; preferably at least 75° C.; more preferably at least 100° C.; even more preferably at least 150° C. This heat may emanate from any suitable source such as, for example, a hair dryer.

The means for physically smoothing hair can be any apparatus capable of physically smoothing the hair such as, for example, a hair brush or comb.

In a preferred embodiment, the means for smoothing hair also serves as the source for generating heat such as, for example, a flat iron. The heating temperature using a flat iron can range from 150 to 200° C.

In another embodiment of the present invention, the process for straightening or relaxing hair may be repeated several times in order to achieve the desired degree of curl removal from the hair. This can be performed by re-dampening or re-wetting the hair with the inventive composition before straightening or relaxing the hair using heat, and then optionally physically smoothing the hair each time.

Due to the absence of harsh hydroxide-containing compounds, a barrier substance is not required when using the hair straightening/relaxing composition of the present invention. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. A barrier substance is not necessary when using the process and composition of the present invention.

The present invention will be better understood from the examples that follow, all of which are intended for illustrative purposes only, and are not meant to unduly limit the scope of the invention in any way.

EXAMPLES

In all examples hereunder, the quantities of ingredients are indicated in amounts by weight of active matter, except if expressly otherwise stated.

Examples 1 and 2

In these examples, the straightening effect of the compositions of the present invention was tested on hair with natural tight curls, using the following General Procedure:

The tests were done on hair swatches made of approximately 400 strands of hair, 7 cm long (full length when straight). The following treatment steps were performed:
 (1) The hair swatches were soaked in various dicarboxylic acid solutions overnight then blotted dry once with paper towel, and
 (2) The damp hair was then straightened by passing a flat iron at about 190° C. over the hair 5 times, 6-7 seconds each pass.

After the treatments, as defined above, the straightened hair swatches were shampooed with a 10% by weight ammonium lauryl sulfate (pH=6.0) solution in water two times (2 minutes of shampooing and 3 minutes of rinsing each time at 40° C.). The final length of the hair was measured when the hair was completely dry at ambient conditions.

The hair straightening effect of the inventive compositions was characterized according to the final length of the hair swatches after treatment with one or more cycles compared to the initial length of the hair swatches. The following notations were used:

A=initial length of hair in the naturally curly state measured (cm); B=final length measured (cm). The higher the B value is, the more straightened the hair is.

Comparative Example 1

Comparison Between the inventive compositions containing a dicarboxylic acid and conventional lye and no-lye relaxers.

Example 1A

Straightening Effect

The following example show the measured lengths of the hair swatches before and after treatment with the inventive compositions using the General Procedure above, at various levels of maleic acid.

The hair was treated with 0.1%, 0.5%, 1%, 2%, and 5% by weight solutions of buffered maleic acid in water with and without 1% by weight guanidine carbonate overnight. The damp hair was flat ironed, washed and rinsed as described in the General Procedure above. The data is shown below in Table 1.

TABLE 1

| Carboxylic Acid levels (% by weight) | 0.1% | 0.5% | 1% | 2% | 5% |
|---|---|---|---|---|---|
| Maleic acid disodium hydrate (pH = 9.6 to 9.7) | | | | | |
| A = Initial swatch length (cm) | 3.25 | 3.5 | 3.5 | 3.5 | 4.0 |
| B = Final swatch length (cm) | 5.5 | 6.0 | 6.0 | 6.5 | 7.0 |
| Maleic acid disodium hydrate and 1% guanidine carbonate (pH = 10) | | | | | |
| A = Initial swatch length (cm) | 3.0 | 3.0 | 3.25 | 3.5 | 3.25 |
| B = Final swatch length (cm) | 5.0 | 5.25 | 6.2 | 7.2 | 6.0 |

The results above show that the curl of the fibers was effectively modified toward straightened hair by the use of the dicarboxylic acid formula coupled with the heat.

For purposes of comparison, the hair was treated with conventional commercial lye and no-lye relaxers at mild, medium and coarse strengths (pH>13), containing hydroxide compounds in a classical aqueous cosmetically acceptable medium, with the following concentrations:

Classical No-Lye Relaxers:

| | Concentration of active (% by weight) | |
|---|---|---|
| Strength | Potassium hydroxide | Guanidine hydroxide |
| Fine | 2.80 | |
| Medium | | 4.81 |
| Coarse | | 5.08 |

Classical Lye Relaxers:

| Strength | Concentration of active (% by weight) Sodium hydroxide |
|---|---|
| Fine | 2.10 |
| Medium | 2.25 |
| Coarse | 2.375 |

These commercial lye and no-lye relaxers showed comparable straightening effects on hair (see Table 2 below); however, these products are generally damaging to the hair and to the scalp. Therefore, the data in Table 1 above show comparable and even better straightening effects without compromising or significantly reducing hair quality.

TABLE 2

| | A = initial length (cm) | B = final length (cm) |
|---|---|---|
| With no-lye: | | |
| coarse | 3.75 | 6.5 |
| medium | 3.5 | 6.4 |
| fine | 3.5 | 6.4 |
| With lye: | | |
| coarse | 3.75 | 6.25 |
| medium | 3.5 | 6.1 |
| fine | 3.75 | 6.75 |

Example 1B

Porosity Test

The hair treated with the inventive compositions as described showed no or very little damage after the treatment versus hair treated with the conventional lye or no-lye relaxers as described above.

Hair damage was measured using a porosity test described as follows:

The quality of the hair fibers was examined by inspecting their porosity after treatment. The porosity indicates if a treatment negatively affects the integrity or quality of hair, which represents the amount of damage to the hair fibers. This can be determined from microscopic images of the cross sections of virgin (chemically untreated) and treated hair fibers pre-soaked with a fluorescent dye (sulforhodamine B stain). The diffusion of the dye in the fiber indicates how porous the fiber has become after treatment.

This porosity test showed that hair treated with the various dicarboxylic acids compositions as described in example 1A above exhibited a similar level of porosity as virgin hair, whereas fibers treated with the typical lye relaxers showed greater amounts of dye diffusion. A greater amount of dye diffusion indicates a higher porosity level and a more negative effect on the quality of the hair. The results from the porosity test of the present invention indicate that the dicarboxylic acid treatment does not negatively affect the quality of the fiber compared to commercial lye relaxers.

Comparative Example 2

Effect of pH

The hair was treated with 1%, 2%, 4%, and 5% by weight solutions of acetic acid and sodium trichloroacetate in water (with and without guanidine carbonate) overnight, flat ironed, washed and rinsed following the General Procedure above. The initial and final swatch lengths are shown below in Table 3.

TABLE 3

| Carboxylic Acid levels (% by weight) | 1% | 2% | 4% | 5% |
|---|---|---|---|---|
| Acetic acid (pH = 2.1 to 2.5) | | | | |
| (A = Initial swatch length cm) | 3.0 | 3.25 | 3.0 | 3.0 |
| (B = Final swatch length cm) | 3.5 | 3.6 | 3.5 | 3.4 |
| Acetic acid and 1% by weight guanidine carbonate (pH = 3.4 to 4.3) | | | | |
| (A = Initial swatch length cm) | 3.25 | 3.0 | 2.9 | 3.2 |
| (B = Final swatch length cm) | 3.5 | 3.5 | 3.25 | 3.3 |
| Sodium trichloroacetate (pH = 4.5 to 5.6) | | | | |
| (A = Initial swatch length cm) | 3.5 | 4.0 | 4.0 | 3.75 |
| (B = Final swatch length cm) | 3.9 | 4.2 | 4.2 | 3.9 |
| Sodium trichloroacetate and 1% by weight guanidine carbonate (pH = 11) | | | | |
| (A = Initial swatch length cm) | 3.5 | 3.75 | 3.6 | 3.5 |
| (B = Final swatch length cm) | 6.0 | 6.25 | 5.9 | 6.0 |

The results above show that the hair was significantly less straightened, if at all, by the use of a composition containing a carboxylic acid (monocarboxylic acid) at low pH values. However, the composition containing a monocarboxylic acid at the higher pH value resulted in greater hair straightening.

An additional benefit to the hair treated with the inventive compositions was the reduction in volume of the body of the hair leading to greater manageability and less frizziness of the hair.

Examples 3 to 6

In these examples, the straightening effect of the gel compositions of the present invention was tested on hair with natural tight curls, using the following General Procedure:

The tests were done on hair swatches made of approximately 250 mg of hair. The following treatment steps were performed:

(1) The hair swatches were treated with 7 g each of the gel formulas; the gel formulas were applied evenly onto the hair and left on the hair for about 20 minutes, and (2) The damp hair was then straightened by passing a hot flat-iron (ceramic Infrashine hot iron at 180 to 200° C.) over the hair 5 times, 6-7 seconds each pass. Prior to each hot iron pass, the hair was re-wet with the gel formulas just enough to coat the surface of the hair.

After the treatments, as defined above, the straightened hair swatches were shampooed with a 10% by weight ammonium lauryl sulfate (pH=6.0) solution in water two times (2 minutes of shampooing and 3 minutes of rinsing each time at 40° C.). The final length of the hair was measured when the hair was completely dry at ambient conditions.

Note that one treatment process (treat-heat-wash-rinse) as described above constitutes one treatment cycle. This cycle may be repeated any number of times to achieve the desired degree of straightness.

The hair straightening effect of the inventive compositions was characterized according to the final length of the hair swatches after treatment with one or more cycles compared to the initial length of the hair swatches. The following notations were used:

A=initial length of hair in the naturally curly state measured (cm); B=final length measured (cm). The higher the B value is, the more straightened the hair is.

Example 3

The following example show the measured lengths of the hair swatches before and after treatment with the inventive compositions using the General Procedure above, at various levels of maleic acid.

The hair was treated with various dicarboxylic acid gel formulas having a pH of 11 and containing from 1% to 5% by weight of DL-maleic acid disodium salt (Sigma-Aldrich), 4% by weight of Polyquaternium-37 (Ultragel 300 from Cognis), 1% by weight of guanidine carbonate, 1% by weight of glycerin, and water (qsp 100%).

The damp hair was treated, flat ironed, washed and rinsed as described in the General Procedure above, two times (two cycles). The results obtained are shown in the two tables hereunder:

$1^{st}$ Cycle

| Concentration % of maleic acid | A = initial length (cm) | B = final length (cm) |
| --- | --- | --- |
| 1 | 3.5 | 5.5 |
| 2 | 3.5 | 5.75 |
| 5 | 4.0 | 5.5 |

$2^{nd}$ Cycle

| Concentration % of maleic acid | A = initial length (cm) | B = final length (cm) |
| --- | --- | --- |
| 1 | 5.5 | 7.2 |
| 2 | 5.75 | 7.75 |
| 5 | 5.5 | 7.2 |

After the $1^{st}$ cycle above, significant straightening of the hair was achieved. After the $2^{nd}$ cycle, the hair was even more straightened. At 1% and 2% maleic acid, where the lengths of the treated hair were twice the initial lengths, the hair can be characterized as being completely straightened.

The conventional lye and no-lye relaxers as described in example 1 above at mild, medium and coarse strengths (pH>13) showed comparable straightening effects on hair (final lengths ranging from about 6.1 to about 6.75 cm and initial lengths of the hair ranging from about 3.5 to about 3.75 cm); however, these products are generally damaging to the hair.

The results above show that the curl of the fibers was effectively modified toward straightened hair by the use of the dicarboxylic acid gel formula of the present invention coupled with the heat. Therefore, the data in the table above show comparable and even better straightening effects without compromising or significantly reducing hair quality.

Example 4

Example 3 was repeated, using gel formulas having a pH of 11 and containing 2% by weight DL-maleic acid disodium salt (Sigma-Aldrich), various levels of polyquaternium-37 (Ultragel 300 from Cognis), 1% by weight guanidine carbonate, 1% by weight glycerine, and water (qsp 100%).

The resultant hair straightening data is presented below:

| % of Polyquaternium-37 | A = initial length (cm) | B = final length after $1^{st}$ treatment cycle | B = final length (cm) (cm) after 2nd treatment cycle |
| --- | --- | --- | --- |
| 2.5 | 3.5 | 5.0 | 6.8 |
| 3 | 3.5 | 5.0 | 6.7 |
| 3.5 | 4.2 | 4.8 | 7.2 |
| 4 | 3.9 | 4.2 | 6.7 |
| 4.5 | 4.0 | 5.3 | 7.3 |
| 5 | 3.8 | 5.0 | 7.1 |

The results above show that the hair was significantly straightened at various levels of Polyquaternium-37 in the inventive compositions, indicating desirable straightening benefits to hair.

Example 5

Effect of pH

Example 3 was repeated, using a base gel formula containing 4% by weight of polyquaternium-37 (Ultragel 300 from Cognis), 1% by weight of glycerine, and water (qsp 100%), and containing or not 2% by weight of DL-maleic acid disodium salt (Sigma-Aldrich) and 2% by weight of various amines. The hair swatches underwent two treatment cycles.

The resultant hair straightening data is presented below:

| Gel composition | pH | Initial swatch length (cm) | Final swatch length (cm) after $2^{nd}$ cycle |
| --- | --- | --- | --- |
| Base = 4% Polyquaternium-37 + 1% glycerine (control) | 4.2 | 8.5 | 8 |
| Base + 2% maleic acid salt (control) | 7.5 | 7.5 | 7.5 |
| Base + 2% 2-amino-2-methyl-1-propanol (control) | 11.1 | 8.0 | 10.0 |
| Base + 2% maleic acid salt + 2% 2-amino-2-methyl-1-propanol | 11.1 | 6.5 | 14.0 |
| Base + 2% maleic acid salt + 2% triethanolamine | 9.4 | 7.6 | 11.7 |
| Base + 2% maleic acid salt + 2% N,N-dimethylethanol amine | 10.8 | 8.0 | 14.0 |

The results above show that the hair was significantly straightened with the gel compositions containing both maleic acid disodium salt and an amine at pH levels between 9 and 11. The control gels without maleic acid disodium salt and/or with pH levels below 7.5 had little to no effects on reducing the curl.

Example 6A

Porosity Test

Damage of the hair treated with the various dicarboxylic acid gel formulas of examples 3A and 3B using the process of the invention, was evaluated using the porosity test described in example 1B above.

The results showed that the hair treated with the gel formulas of examples 3A and 3B exhibited a similar level of porosity as virgin hair, whereas fibers treated with the classical lye relaxer showed greater amounts of dye diffusion. The results from the porosity test therefore indicate that the dicarboxylic acid gel formula treatment does not negatively affect the quality of the fiber compared to commercial lye relaxers.

Example 6B

Permanent Straightening

The same hair swatches straightened by the dicarboxylic acid gel treatments as described in examples 3, 4 and 5 above were shampooed ten times over the course of a month and stored in a temperature and humidity controlled chamber at 25° C.±0.5° C. and 45%±2% humidity (mean standard deviation). Similar tests for permanent straightening were performed using gel formulas replacing maleic acid with other dicarboxylic acids such as malic acid, pyruvate sodium salt and citrate sodium salt, each at 2% by weight.

After ten shampoos, the hair swatches remained straightened and continued to remain straightened after two months, signifying a permanent transformation of the hair fibers.

Example 6C

Aesthetic Properties

Three hair swatches with tight curls from two panelists (total of 6 swatches) were straightened using the General Procedure above with three different compositions: a commercial relaxer product as described in example 1 above, and two dicarboxylic acid gel formulas having a pH of 10.7 and comprising (i) 2% by weight of maleic acid, 1% by weight of guanidine carbonate and 4% by weight of Polyquaternium-37 and (ii) 2% by weight of maleic acid, 0.2% by weight of urea, 1% by weight of guanidine carbonate and 4% by weight of Polyquaternium-37. Using key attributes as evaluated by a total of 6 cosmetologists, the swatches treated with the dicarboxylic acid gel formulas performed as well or better than the swatches treated with the commercial relaxer product in terms of combing, straightness, suppleness, tactile and visual smoothness, and coating. In addition, the swatches treated with the dicarboxylic acid gel formulas of the present invention showed better comparable straightening compared to the swatches treated with the commercial relaxer product.

An additional benefit to the hair treated with the inventive compositions was the reduction in volume of the body of the hair leading to greater manageability and less frizziness of the hair.

The invention claimed is:

1. A process for straightening or relaxing hair, comprising the following steps:
    (a) providing a hair straightening or relaxing composition having a pH ranging from 8 to 11.5, and containing, in a cosmetically acceptable medium, at least one weak acid chosen from monocarboxylic, dicarboxylic and tricarboxylic acids, their salts, and mixtures thereof, and at least one denaturant capable of disrupting hydrogen bonds in the hair, in an amount of from 0.1% to 25% by weight, based on the total weight of the composition;
    (b) contacting the hair with the hair straightening or relaxing composition to form treated hair; and
    (c) straightening or relaxing the treated hair by applying heat, wherein hydroxide-containing compounds are not used.

2. The process of claim 1, wherein the hair straightening or relaxing composition used in step (a) has a pH of at least 9 and up to 11.

3. The process of claim 1, wherein the at least one weak acid is chosen from dicarboxylic acids.

4. The process of claim 1, wherein the at least one weak acid is employed in the hair straightening or relaxing composition in an amount of from 0.1% to 50% by weight, based on the total weight of the composition.

5. The process of claim 1, wherein the hair straightening or relaxing composition used in step (a) further contains at least one viscosity modifying agent.

6. The process of claim 5, wherein the viscosity modifying agent is chosen from:
    (a) cationic polymers;
    (b) polysaccharides or polysaccharide derivatives;
    (c) homopolymers and copolymers of carboxyvinyl monomers.

7. The process of claim 1, wherein step (c) is performed with simultaneous use of means for smoothing hair at a temperature of at least 100° C.

8. A process for straightening or relaxing hair, comprising the following steps:
    (a) providing a hair straightening or relaxing composition having a pH ranging from 8 to 11.5, and containing, in a cosmetically acceptable medium, at least one weak acid chosen from monocarboxylic, dicarboxylic and tricarboxylic acids, their salts, and mixtures thereof, wherein the at least one weak acid is chosen from malic acid, maleic acid, itaconic acid, oxalic acid, malonic acid, mesoxalic acid, fumaric acid, succinic acid, tartaric acid, alpha-ketoglutaric acid, iminodiacetic acid, galactartic acid, adipic acid, glutaric acid, their salts, and mixtures thereof;
    (b) contacting the hair with the hair straightening or relaxing composition to form treated hair; and
    (c) straightening or relaxing the treated hair by applying heat, wherein hydroxide-containing compounds are not used.

9. The process of claim 1, wherein the amount of the at least one weak acid is from 0.5% to 20% by weight, based on the total weight of the composition.

10. The process of claim 1, wherein the amount of the at least one weak acid is from 0.5% to 10% by weight, based on the total weight of the composition.

11. The process of claim 5, wherein the amount of the at least one viscosity modifying agent is from 0.1% to 10% by weight, based on the total weight of the composition.

12. The process of claim 1, wherein the at least one viscosity modifying agent is chosen from the group consisting of celluloses and derivatives thereof; xanthan gum, guar gum; starch and starch derivatives.

13. The process of claim 1, wherein step (c) is performed with simultaneous use of means for smoothing using a flat iron having a heating temperature ranging from 150 to 200° C.

14. The process of claim 6 wherein said viscosity modifying agent comprises polyquaternium-37.

* * * * *